(12) United States Patent
Ukawa et al.

(10) Patent No.: US 11,166,665 B2
(45) Date of Patent: Nov. 9, 2021

(54) INDEX OUTPUT DEVICE, INDEX OUTPUT METHOD, AND INDEX OUTPUT PROGRAM

(71) Applicant: Nihon Kohden Corporation, Tokyo (JP)

(72) Inventors: Teiji Ukawa, Tokyo (JP); Kazuya Nagase, Tokyo (JP)

(73) Assignee: Nihon Kohden Corporation, Tokyo (JP)

(*) Notice: Subject to any disclaimer, the term of this patent is extended or adjusted under 35 U.S.C. 154(b) by 367 days.

(21) Appl. No.: 16/078,899

(22) PCT Filed: Feb. 3, 2017

(86) PCT No.: PCT/JP2017/004099
§ 371 (c)(1),
(2) Date: Aug. 22, 2018

(87) PCT Pub. No.: WO2017/145715
PCT Pub. Date: Aug. 31, 2017

(65) Prior Publication Data
US 2019/0059808 A1 Feb. 28, 2019

(30) Foreign Application Priority Data
Feb. 23, 2016 (JP) .............................. JP2016-032385

(51) Int. Cl.
*A61B 5/00* (2006.01)
*A61B 5/369* (2021.01)
(Continued)

(52) U.S. Cl.
CPC ............ *A61B 5/4821* (2013.01); *A61B 5/369* (2021.01); *A61B 5/4824* (2013.01); *A61B 5/742* (2013.01);
(Continued)

(58) Field of Classification Search
None
See application file for complete search history.

(56) References Cited

U.S. PATENT DOCUMENTS 6,315,736 B1 11/2001 Tsutsumi et al.
8,983,613 B2 3/2015 Kamataki et al.
(Continued)

FOREIGN PATENT DOCUMENTS

JP 2006326050 A 12/2006

OTHER PUBLICATIONS

Hager et al. The Perfusion Index as Measured by a Pulse Oximeter Indicates Pain Stimuli in Anesthetized Volunteers. Anesthesiology. 2004; 101 :A514. (Year: 2004).*
(Continued)

*Primary Examiner* — Etsub D Berhanu
(74) *Attorney, Agent, or Firm* — Faegre Drinker Biddle & Reath LLP

(57) ABSTRACT

An index output device for appropriately evaluating the conditions of the patient under anesthesia. An index output device 100 includes an electric stimulation section 170, an acquisition section 180, a calculation section, and an output section. The electric stimulation section 170 is configured to apply an electric stimulus to a living body. The acquisition section 180 is configured to acquire a plurality of physiological responses from the living body in response to the common electric stimulus applied to the living body by the electric stimulation section 170. The calculation section is configured to calculate, from the plurality of responses of the living body acquired by the acquisition section, an index related to a level of muscular relaxation (TOF) and an index related to a level of analgesia (PIR). The output section is configured to output the indexes calculated by the calculation section.

9 Claims, 4 Drawing Sheets

(51) Int. Cl.
  *A61B 5/021* (2006.01)
  *A61B 5/374* (2021.01)
  *A61B 5/377* (2021.01)

(52) U.S. Cl.
  CPC ......... *A61B 5/7445* (2013.01); *A61B 5/02116* (2013.01); *A61B 5/374* (2021.01); *A61B 5/377* (2021.01)

(56) References Cited

U.S. PATENT DOCUMENTS

| | | | | |
|---|---|---|---|---|
| 2004/0079372 | A1* | 4/2004 | John | A61B 5/374 128/204.18 |
| 2004/0254617 | A1* | 12/2004 | Hemmerling | A61B 7/006 607/48 |
| 2005/0010116 | A1* | 1/2005 | Korhonen | A61B 5/4035 600/481 |
| 2006/0217615 | A1 | 9/2006 | Huiku et al. | |
| 2006/0270943 | A1* | 11/2006 | Kamataki | A61B 5/0488 600/554 |
| 2009/0005703 | A1* | 1/2009 | Fasciano | A61B 5/7445 600/561 |
| 2009/0198147 | A1* | 8/2009 | Ono | A61B 5/0285 600/554 |
| 2011/0137134 | A1 | 6/2011 | Hemmerling et al. | |
| 2012/0197146 | A1 | 8/2012 | Tan et al. | |
| 2012/0330167 | A1* | 12/2012 | Gaw | A61B 5/0537 600/481 |
| 2015/0103095 | A1 | 4/2015 | Suzuki et al. | |
| 2015/0342485 | A1* | 12/2015 | Hertel | A61B 5/0472 600/523 |

OTHER PUBLICATIONS

Skowno, J.J. Perfusion index changes during emergence from anaesthesia in children. Anaesthesia and Intensive Care, vol. 41, No. 4, Jul. 2013. (Year: 2013).*

Seitsonen et al. EEG spectral entropy, heart rate, photoplethysmography and motor responses to skin incision during sevoflurane anaesthesia. ACTA Anaesthesiol Scand 2005; 49; 284-292. (Year: 2005).*

Seitsonen et al. EEG, Heart Rate, Pulse Plethysmography and Movement REsponses to Skin Incision. Anesthesiology, vol. 96 Sup 2, Sep. 2002, p. A582. (Year: 2002).*

International Search Report for PCT/JP2017/004099 dated Jun. 27, 2017.

Written Opinion of the International Searching Authority for PCT/JP2017/004099 dated Jun. 27, 2017.

* cited by examiner

[Fig. 1]
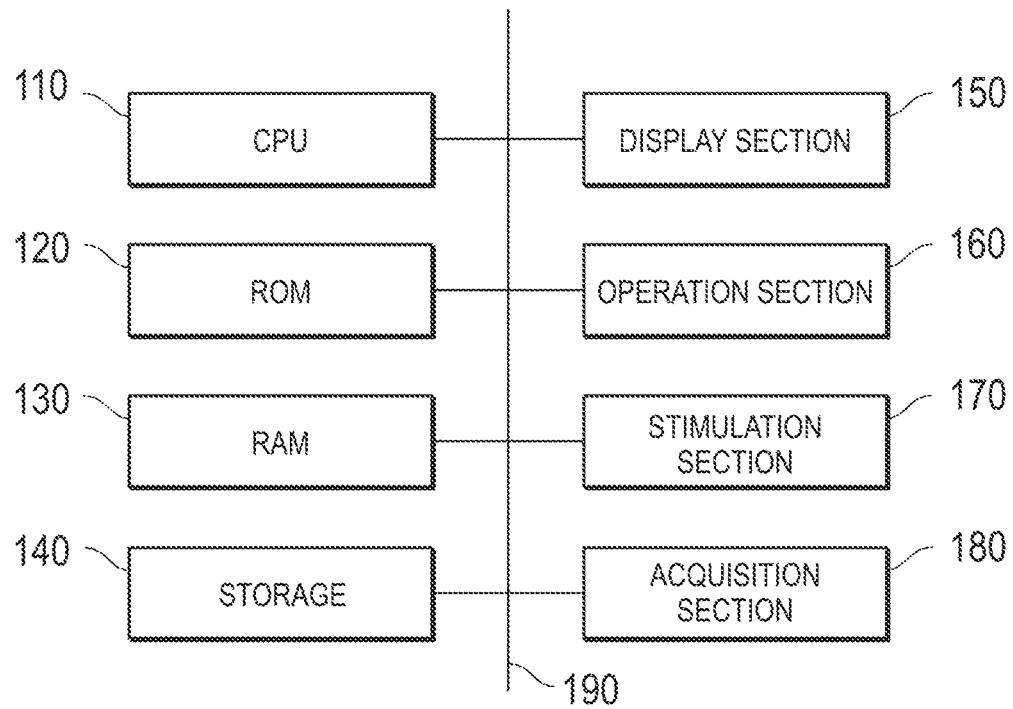
[Fig. 2]
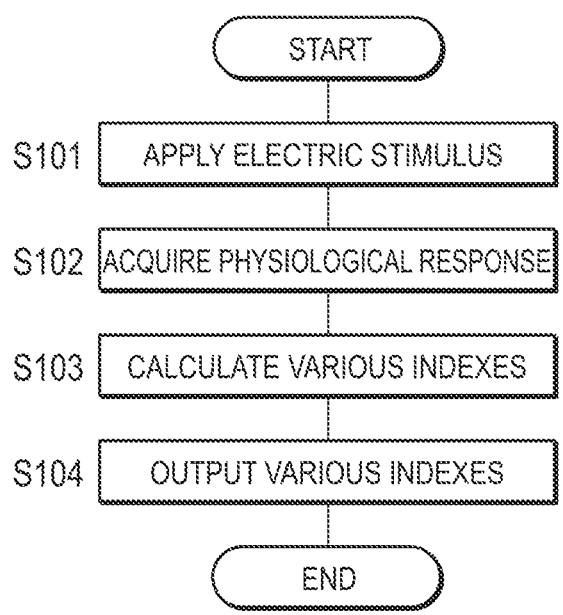

[Fig. 3]
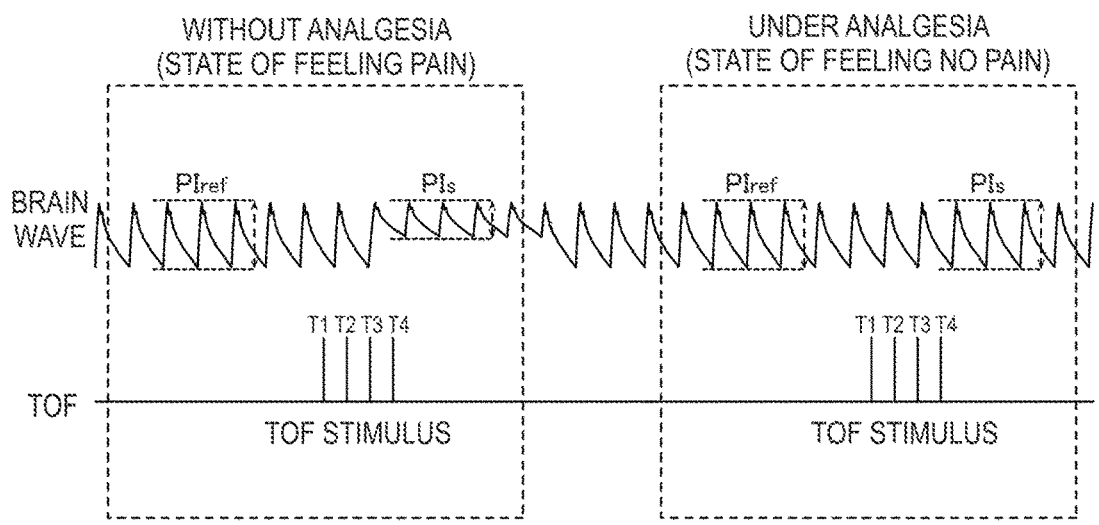
[Fig. 4]
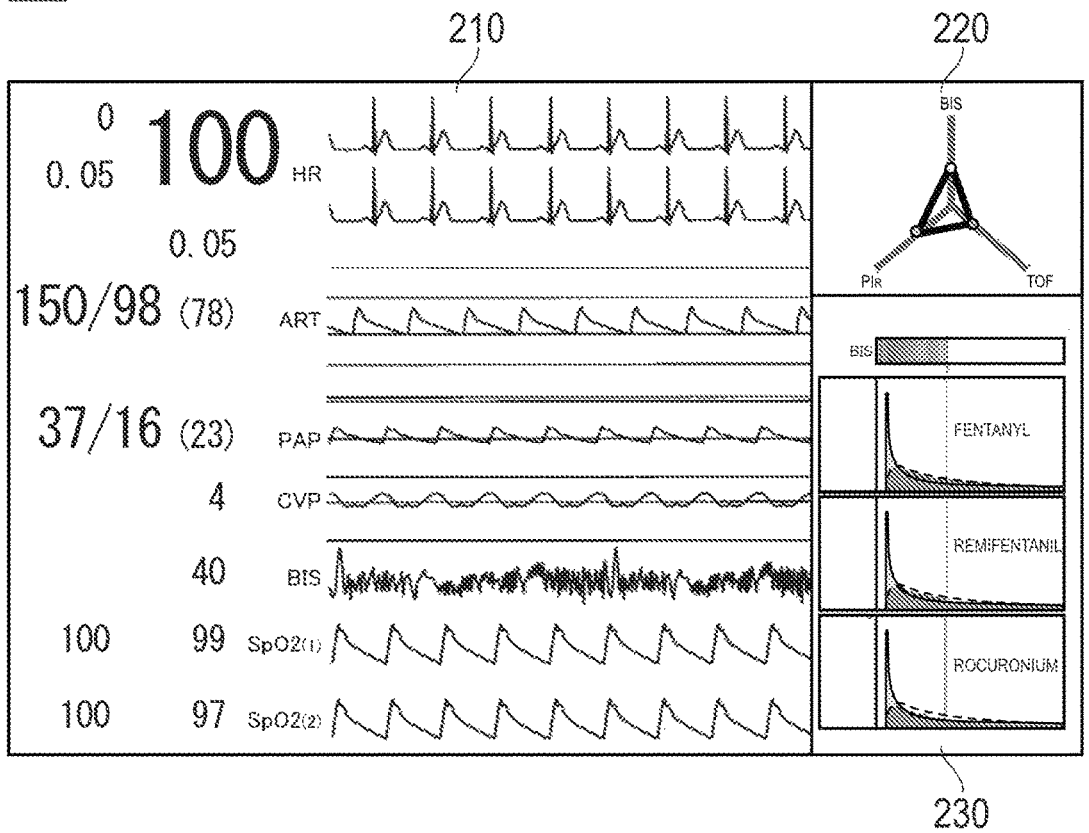

[Fig. 5]
220
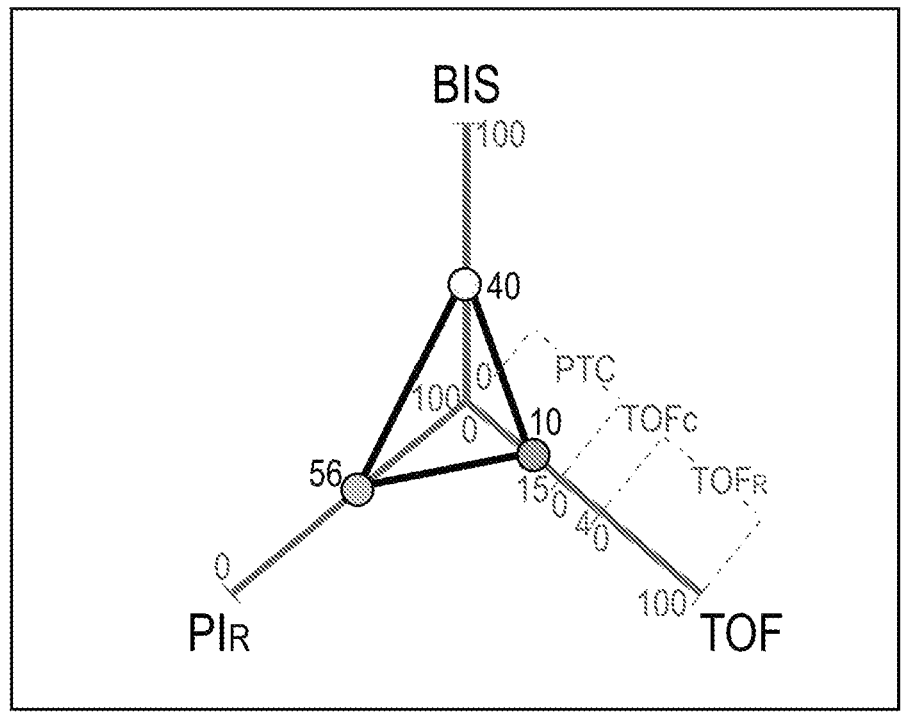
[Fig. 6]
220
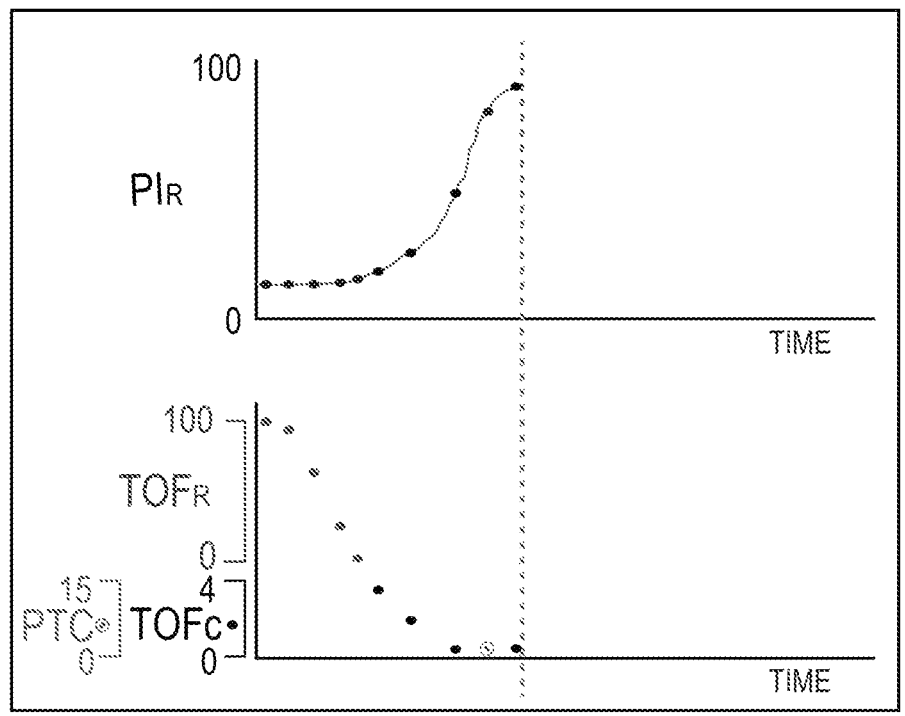

[Fig. 7]
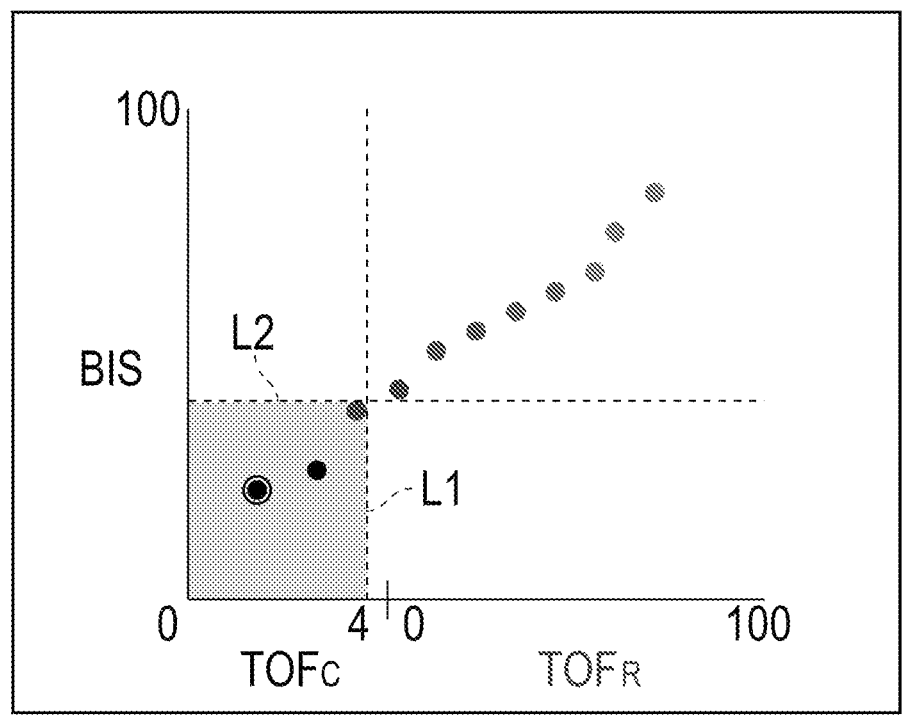

INDEX OUTPUT DEVICE, INDEX OUTPUT METHOD, AND INDEX OUTPUT PROGRAM

CROSS-REFERENCE TO RELATED APPLICATIONS

This application is a national stage application (under 35 U.S.C. § 371) of PCT/JP2017/004099, filed Feb. 3, 2017, which claims benefit of Japanese Application No. 2016-032385, filed Feb. 23, 2016, both of which are incorporated herein by reference in their entirety.

TECHNICAL FIELD

The presently disclosed subject matter relates to an index output device, an index output method, and an index output program.

BACKGROUND ART

Three important factors for controlling the conditions of a patient in performing anesthesia to patients are sedation, muscular relaxation, and analgesia. As a technique for evaluating the state of sedation among these three factors, a monitoring technique of BIS (Bispectral Index) for measuring a level of the sedation by spectral analysis of EEG has been known. As a technique for evaluating the state of muscular relaxation, a monitoring technique of TOF (Train of Four) for measuring a level of the muscular relaxation on the basis of response of muscles to an electric stimulus to the muscles has been known (for example, Japanese Patent Publication No. 2006-326050).

But, a technique for evaluating the state of analgesia, which is the remaining one of the factors, has not been established, so that analgesia monitoring relies mostly on experiences of doctors or the like in charge of anesthesia. Regarding this problem, studies have been carried out recently on relationship between a PI (Perfusion Index), which is an index indicating a perfusion state of blood at a fingertip or the like, and a level of pain that a patient feels. For example, in a case where a patient feels a pain by a stimulus from a surgical operation or the like, the perfusion of blood at a fingertip is down-regulated due to sympathetic nerve stimulus, whereby the PI is reduced. Meanwhile, when a patient does not feel a pain, the down-regulation of the perfusion of blood due to the sympathetic nerve stimulus, and the consequent PI reduction will not occur. As such, it has been reported that there is a relationship between the PI and the level of pain that the patient feels. Moreover, it has been studied to determine, by measuring the PI, whether a patient feels a pain.

However, the simply measuring the PI of a patient as above does not make it possible to evaluate the level of analgesia, while making it possible to determine whether the patient feels a pain at the time of the measurement. For example, a high PI value at a certain point does not make it possible to determine whether the cause of the high PI value is because the stimulus from such as an operation or the like is weak at the time, or because the analgesia is appropriately carried out. Because of this, quantitative and periodic monitoring of the state of analgesia is not possible, and thus it could be impossible to appropriately evaluate the conditions of the patient under anesthesia while treating the patient.

SUMMARY OF INVENTION

The presently disclosed subject matter has been accomplished in view of the aforementioned circumstances, and an object of the presently disclosed subject matter is to provide an index output device, an index output method, and an index output program for appropriately evaluating the conditions of the patient under anesthesia.

The object can be attained by the following configurations.

A first aspect of the presently disclosed subject matter is an index output device, including an electric stimulation section, an acquisition section, a calculation section, and an output section. The electric stimulation section is configured to apply an electric stimulus to a living body. The acquisition section is configured to acquire a plurality of physiological responses from a living body in response to the common electric stimulus applied to the living body by the electric stimulation section. The calculation section is configured to calculate, from the plurality of responses of the living body thus acquired by the acquisition section, an index related to a level of muscular relaxation and an index related to a level of analgesia. The output section is configured to output the calculated indexes.

A second aspect of the presently disclosed subject matter is an index output device including an acquisition section, a calculation section, and an output section. The acquisition section is configured to acquire a plurality of physiological responses of a living body. The calculation section is configured to calculate at least two indexes from among an index related to a level of muscular relaxation, an index related to a level of analgesia, and an index related to a level of sedation, from the plurality of responses of the living body thus acquired by the acquisition section. The output section is configured to output, in association with each other, the calculated indexes.

A third aspect of a presently disclosed subject matter is an index output method including an electric stimulation step, an acquisition step, a calculation step, and an output step. The electric stimulation step includes applying an electric stimulus to a living body. The acquisition step includes acquiring a plurality of physiological responses from a living body in response to the common electric stimulus applied to the living body in the electric stimulation step. The calculation step includes calculating, from the plurality of responses of the living body thus acquired in the acquisition step, an index related to a level of muscular relaxation and an index related to a level of analgesia. The output step includes outputting the indexes thus calculated in the calculation step.

A fourth aspect of a presently disclosed subject matter is an index output program for causing a computer to perform an electric stimulation step, an acquisition step, a calculation step, and an output step. The electric stimulation step includes applying an electric stimulus to a living body. The acquisition step includes acquiring a plurality of physiological responses from a living body in response to the common electric stimulus applied to the living body in the electric stimulation step. The calculation step includes calculating, from the plurality of responses of the living body thus acquired in the acquisition step, an index related to a level of muscular relaxation and an index related to a level of analgesia. The output step includes outputting the indexes thus calculated in the calculation step.

BRIEF DESCRIPTION OF DRAWINGS

FIG. 1 illustrates a schematic structure of an index output device according to one embodiment of a presently disclosed subject matter.

FIG. 2 is a flowchart illustrating steps of a process performed by the index output device.

FIG. 3 is a view illustrating relationship between a TOF stimulus and a PI ratio.

FIG. 4 illustrates one example of a monitoring screen displayed on the index output device.

FIG. 5 illustrates one example of an index display section of the monitoring screen.

FIG. 6 is a view illustrating how changes in various indexes are plotted in time series on the index display section of the monitoring screen.

FIG. 7 is a view illustrating how values of various indexes are plotted in time series on a 2-dimensional coordinate system on the index display section of the monitoring screen.

DESCRIPTION OF EMBODIMENTS

In the following, one embodiment of the presently disclosed subject matter will be described, referring to the drawings attached herewith. Note that identical elements are given identical reference numerals in the explanation on the drawings, and the redundant explanation will not be repeated. The dimensional ratio in the drawings may be exaggerated for the sake of easy explanation, and may be different from the actual dimensional ratio.

FIG. 1 illustrates a schematic structure of an index output device according to one embodiment of a presently disclosed subject matter.

As illustrated in FIG. 1, an index output device 100 includes a CPU 110, a ROM 120, a RAM 130, a storage 140, a display section 150, an operation section 160, a stimulation section 170, and an acquisition section 180, which are connected with each other via a bus 190 for communicating signals therebetween.

The CPU 110 is configured to perform control and various computing processes of the aforementioned sections according to a program stored in the ROM 120 or the storage 140. The CPU 110 functions as a calculation section and an output section by executing the program. The ROM 120 is configured to store various programs and various data. THE RAM 130 is configured to temporally store a program and data while serving as a working area.

The storage 140 is configured to store various programs (including an operating system), and various data.

The display section 150 may be a liquid crystal display for example, and is configured to display information such as biological information of a patient, various indexes calculated, and the like.

The operation section 160 is used for inputting various inputs. The operation section 160 includes operation keys realized as software on the display section 150 serving as a touch panel, and operation buttons provided as hardware.

The stimulation section 170 is connected with a terminal for applying an electric stimulus to a patient, and is configured to apply electric stimuli in plural patterns to the patient via the terminal. For example, the stimulation section 170 may be configured to apply an electric stimulus for monitoring a TOF (hereinafter, this stimulus is referred to as a TOF stimulus) to an ulnar nerve of a patient via an electrode clip attached to an arm of the patient. The stimulation section 170 may impart the TOF stimulus to the site excluding the ulnar nerve, and may impart the TOF stimulus to a plurality of sites via a plurality of terminals.

The acquisition section 180 is connected with various sensors or the like for detecting a plurality of physiological responses of the patient, and is configured to acquire the plurality of physiological responses, such as brain waves, muscular reactions, and pulse waves, of the patient. For example, the acquisition section 180 may be configured to acquire brain waves of the patient via electrodes attached to a head of the patient. Moreover, the acquisition section 180 may be configured to acquire, via an acceleration sensor attached to a palm of the patient, reactions that an adductor muscle of a thumb of the patient makes in response to electric stimulation applied by the stimulation section 170. Moreover, the acquisition section 180 may be configured to acquire pulse waves of the patient via a pulse oximetry sensor attached to a fingertip or the like of the patient.

The index output device 100 may include a constituent element other than the constituent elements mentioned above, and may not include part of the constituent elements mentioned above The index out device 100 according to this embodiment with the configuration as above applies a TOF stimulus to a patient, acquires a plurality of physiological responses, calculates various indexes related to levels of sedation, muscular relaxation, and analgesia from the plurality of physiological responses thus acquired, and outputs the various indexes. In the following, an effect of the index output device 100 will be described.

<Outline of Process of Index Output Device 100>

FIG. 2 is a flowchart illustrating steps of a process performed by the index output device. Each step performed by the index output device 100 illustrated in the flowchart of FIG. 2 is stored as a program in the storage 140 of the index output device 100, and is carried out by the respective sections controlled by the CPU 110.

To begin with, the index output device 100 applies an electric stimulus to a patient as the electric stimulation section (Step S101). More specifically, the CPU 110 of the index output device 100 controls the stimulation section 170 to apply a TOF stimulus to an ulnar nerve of the patient via an electric clip attached to an arm of the patient.

Then, the index output device 100 acquires a physiological reaction of the patient as the acquisition section (Step S102). More specifically, the index output device 100 acquires brain waves of the patient via an electrode attached to a head of the patient. As an alternative, the index output device 100 acquires, via an acceleration sensor attached to a palm of the patient, reactions that an adductor muscle of a thumb of the patient makes. As an alternative, the index output device 100 acquires pulse waves of the patient via a pulse oximetry sensor attached to a fingertip of the patient.

Then, the index output device 100, as the calculation section, calculates an index related to a level of sedation, an index related to a level of muscular relaxation, and an index related to a level of analgesia (Step S103).

More specifically, the index output device 100 calculates a BIS value (an index related to the level of sedation) on the basis of spectral analysis of the brain waves of the patient thus acquired in Step S102. The BIS value is calculated as a numerical value in a range from 0 to 100. A smaller BIS value indicates a higher level of sedation, that is, a deeper hypnoid state of the patient, while a greater BIS value indicates a lower level of sedation, that is, a shallow hypnoid state of the patient.

As an alternative, the index output device 100 calculates a TOF (an index related to the level of muscular relaxation) from a reaction that an adductor muscle of a thumb of the patient makes and that is acquired in Step S102. Examples of the TOF include a TOF ratio, a TOF count, a PTC (Post-Tetanic Count) and the like, which are different from each other in the kinds of the electric stimulus to apply, and the kinds of calculation methods of the index. The TOF will be described later in detail.

As an alternative, the index output device 100 calculates a PI ratio as an index related to the level of analgesia from a wave profile of the pulse waves acquired in Step S102. The PI is a value indicating a level of a pulsating blood amount at a fingertip or the like of a subject, and is calculated based on a pulse wave amplitude acquired by normalizing a pulse component of transmitted light by strength of the transmitted light. Hereinafter, a pulse wave signal normalized by the strength of the transmitted light is referred to as pulse waves. The PI ratio is a ratio between a PI value at a normal time and a PI value when the TOF stimulus is applied. A greater PI ratio indicates a higher level of analgesia, that is, a state in which the patient does not feel a pain, while a smaller PI ratio indicates a lower level of analgesia, that is, a state in which the patient feels a pain. The PI ratio will be described in detail later.

The index output device 100 causes the storage 140 to store therein the various indexes thus calculated above.

Then, the index output device 100 outputs the various indexes as the output section (Step S104). More specifically, the index output device 100 causes the display section 150, to display the various indexes stored in the storage 140 in Step S103 using the monitoring screen 200, for example, as illustrated in FIG. 4. The monitoring screen 200 will be described in detail later.

<Details of PI ratio and TOF>

FIG. 3 is a view illustrating relationship between a TOF stimulus and a PI ratio. FIG. 3 illustrates a change in pulse waves in response to the TOF stimulus applied without analgesia, and a change in pulse waves in response to the TOF stimulus applied under analgesia. Pulse wave amplitude is a value in correlation with the PI. Thus, FIG. 3 illustrates the pulse wave amplitude and the PI in association with each other. In the following, after the PI ratio and TOF are described in detail, the relationship between the TOF stimulus and the PI ratio will be described.

<Regarding the PI Ratio>

The PI ratio is a ratio between the PI value with no stimulus (PIs) and the PI value under TOF stimulus (PIref), and is calculated by an equation "PI ratio=(PIs/PIref)×100." The PI is a value in correlation with the pulse wave amplitude as described above. Therefore, the PI ratio is calculated as a ratio between a pulse wave amplitude at a normal time and a pulse wave amplitude under TOF stimulus. As the pulse wave amplitude at the normal time, a maximum value of the pulse wave amplitude in a predetermined period before the TOF stimulation can be used, for example. Moreover, as the pulse wave amplitude under the TOF stimulus, a minimum value of the pulse wave amplitude in a predetermined period after the TOF stimulation is carried out can be used, for example.

<Regarding TOF>

As illustrated in FIG. 3, the TOF stimulation is carried out by repeating, every 15 seconds, a set of four stimuli T1 to T4 that are successively applied with 0.5 seconds intervals, for example. As described above, the kinds of the TOF include the TOF ratio, the TOF count, the PTC, and the like. The TOF ratio is an index used when the level of muscular relaxation is relatively small. The TOF count and PTC are indexes used when the level of muscular relaxation is relatively large. In the following, the TOF ratio, TOF count, and PTC will be described in detail.

The TOF ratio is a ratio in percentage between a level of the response to the first stimulus T1 and a level of response to the fourth stimulus T4 among the four TOF stimuli. When the muscular relaxation is not carried out, the level of the response to the first stimulus T1 and the level of response to the fourth stimulus T4 are equivalent to each other, so that the TOF ratio becomes 100% in this case. Along with proceeding of the muscular relaxation, the reaction to the fourth stimulus T4 becomes smaller than the reaction to the first stimulus T1, thereby reducing the TOF ratio.

The TOF count is an index used when none of the reactions up to the fourth reaction to the stimuli is detected, or when the reaction to the first stimulus T1 is reduced below 20%. The TOF count is a count obtained by counting the number of detection times of reactions to the successive four stimuli. For example, in a case where three reactions are detected with respect to the four stimuli, the TOF count is 3, and no reaction is detected with respect to the four stimuli, the TOF count is zero.

The PTC is an index used when the muscular relaxation is so deep that TOF count becomes zero. In a case where no reaction is detected even if a stimulus of 1 Hz are applied 15 times (for 15 seconds), the PTC is a count obtained by counting the number of detection times of the reactions with respect to 15-time applications of a single stimulus of 1 Hz (for 15 seconds) applied 3 seconds after a tetanic stimulus that is stronger than the TOF stimulus is applied for 5 seconds. From the PTC count, it is possible to deduce a time when the effect of muscular relaxation is reduced and the TOF count and the TOF ratio are recovered.

<Regarding the Relationship Between the TOF Stimulus and the PI Ratio>

As indicated in the dashed-line frame on the left side of FIG. 3, patients feel a pain with respect to the TOF stimulus when the patients are not under analgesia. Thus, the PI value (PIs) under the TOF stimulus is smaller than the PI value (PIref) at the normal time. Therefore, the PI ratio is small when the patients are not under analgesia. Meanwhile, as indicated in the dashed-line frame on the right side of FIG. 3, patients feel no pain with respect to the TOF stimulus when the patients are under analgesia. Thus, the PI value (PIs) under the TOF stimulus is equivalent to the PI value (PIref) at the normal time, when the patients are under analgesia. Therefore, the PI ratio is large as much as 100%. As such, a greater PI ratio indicates a higher level of analgesia, and a smaller PI ratio indicates a lower level of analgesia. Therefore, by checking the PI ratio, it is possible to evaluate the level of analgesia.

Next, the monitoring screen 200 will be described in detail.

<Monitoring Screen 200>

FIG. 4 illustrates one example of a monitoring screen displayed on the index output device.

As illustrated in FIG. 4, the monitoring screen 200 includes a physiological information display section 210, an index display section 220, and an administration state display section 230.

On the physiological information display section 210, physiological information such as an electrocardiogram, blood pressure, pulmonary arterial blood pressure, central venous pressure, SpO2, body temperature, heart rate, respiratory rate, and/or the like of a patient is displayed, for example. For SpO2, values measured respectively at two sites such as a fingertip and a forehead, for example, are displayed.

On the index display section 220, various indexes acquired in Step S102 in FIG. 2 are displayed in association with each other. The index display section 220 will be described in detail later.

On the administration state display section 230, information regarding a state of administration of a medicine such as fentanyl as an anesthetic agent, remifentanil as an analgesic agent, and rocuronium as a muscle relaxant is displayed. For example, a solid-line graph displayed on the administration state display section 230 indicates a result of simulation regarding a change in blood concentration of a medicine ad-ministered, while a dashed line indicates a result of simulation regarding a change in effect-site concentration of the medicine.

Next, the index display section 220 of the monitoring screen 200 will be described in detail.

<Index Display Section 220>

FIG. 5 illustrates one example of an index display section of the monitoring screen.

As illustrated in FIG. 5, on the index display section 220, various indexes such as the BIS, TOF, and PI ratio (PIR) thus calculated in Step S103 in FIG. 2 are displayed in association with each other. In the example of FIG. 5, the BIS, TOF, and PIR are plotted along three axes extended in three different directions from a common point located at a center portion. The plottings are connected with straight lines and a triangle is formed with each plot serving as a vertex thereof.

The BIS is plotted along an axis on which a point further away from a start point indicates a greater value, that is, an axis on which the start point indicates a minimum value, and an end point indicates a maximum value. Therefore, as the level of sedation becomes greater, the BIS values become smaller, thereby moving the plot from the end point side toward the start point side.

PIR is plotted on an axis on which a point further away from the start point indicates a smaller value, that is, the start point indicates a maximum value, and an end point indicates a minimum value. Therefore, as the level of analgesia becomes greater, the RIR values become smaller, thereby moving the plot from the end point side toward the start point side.

For the TOF, one axis is divided into three portions. The three portions indicate, from an end point side of the axis, TOF ratio (TOFR), TOF count (TOFC), and PTC, respectively. In the respective three portions, a point further away from the start point of the axis indicates a greater value. For example, in the example illustrated in FIG. 5, in the portion indicating TOFR, the edge of the end point side indicates 100, while the edge of the start point side indicates zero. In the portion indicating TOFC, the edge of the end point side of the axis indicates 4, while the edge of the start point side of the axis indicates zero. In the portion indicating PTC, the edge of the end point side indicates 15, while the edge of the start point indicates zero. Therefore, as the level of muscular relaxation becomes greater, the TOFR, TOFC, and PTC values become smaller, thereby moving the plot from the end point side toward the start point side.

In the example of FIG. 5, the BIS value is 40, TOF is 10 in PTC, and PIR is 56. For example, when the levels of sedation, muscular relaxation, and analgesia become greater by, for example, additional administration of a medicine, each plot moves toward the start point located at the center. In this case, the triangle formed by connecting each plot becomes smaller in area. Meanwhile, when the levels of analgesia, muscular relaxation, and analgesia become smaller by, for example, time passage, each plot moves away from the start point. In this case, the triangle becomes larger in area. Therefore, the user can visually and easily evaluate the conditions of the patient under anesthesia by checking the triangle in terms of its size, shape balance, and/or the like.

As described above, the index output device 100 according to this embodiment applies a TOF stimulus to a living body, calculates the TOF and the PI ratio from the reaction of the muscles and the reaction of pulse waves in response to the TOF stimulus, the TOF being an index related to the level of muscular relaxation and the PI ratio being the level of analgesia, and outputs the TOF and PI ratio thus calculated. This enables quantitative and periodic monitoring of the state of analgesia, whereby the conditions of the patient under anesthesia can be evaluated appropriately. Moreover, the TOF stimulus used for acquiring TOF is also used for an input for acquiring the PI ratio, thereby eliminating the need of separately carrying out the input for acquiring the PI ratio, and consequently simplifying a device structure, a control process, and the like.

Moreover, the index output device 100 further calculates, from the brain waves of the living body, an index related to the level of the sedation, and outputs the index thus calculated. With this configuration, the three states of sedation, muscular relaxation, and analgesia, which are important factors in patient control under anesthesia, are collectively evaluated at once; therefore, the conditions of the patient under anesthesia can be evaluated more appropriately.

Moreover, the index output device 100 calculates the PI ratio on the basis of the ratio between the pulse wave amplitude at the normal time and the pulse wave amplitude under electric stimulus. With this configuration, it is possible to easily calculate the PI ratio from a wave profile of the pulse waves.

Moreover, the index output device 100 plots, on the index display section 220 of the monitoring screen 200, various indexes along the axes extended in different directions from a common start point, and display a shape formed by connecting the plotted indexes. With this configuration, the user can visually and easily evaluate the conditions of the patient indicated by the various indexes.

Moreover, the index output device 100 plots, on the index display section 220 of the monitoring screen 200, the PI ratio on the axis on which a point further from the start point indicates a smaller value, and the TOF on the axis on which a point further from the start point indicates a lower level of the muscular relaxation. With this configuration, each plot moves toward the start point side as the levels of muscular relaxation and analgesia become higher; therefore, the shape formed by connecting each plot becomes smaller in area. With this configuration, each plot moves away from the start point side as the levels of muscular relaxation and analgesia become lower; therefore, the shape formed by connecting each plot becomes smaller in area. Therefore, the user can easily evaluate the conditions of the patient by checking the area and balance of the shape formed by the plots.

Moreover, the index output device 100 outputs, in association with each other, at least two indexes from among the index related to the level of sedation, the index related to the level of muscular relaxation, and the index related to the level of analgesia. Therefore, the user can evaluate the plural indexes at glance and easily check relationships between the plural indexes. With this configuration, treatment such as sedation, muscular relaxation, and analgesia can be carried out with a good balance.

<Modification 1>

The embodiment above describes the example in which the BIS, TOF, and PI ratio are displayed on the index display section 220 of the monitoring screen 200 in such a way that the BIS, TOF, and PI ratio are plotted respectively on three axes extended in three different directions from the common start point. However, the display method of the index display section 220 is not limited to this. For example, the respective changes in the various indexes may be displayed by being plotted in time series. In the following, an example in which the changes in the various indexes are displayed by being plotted in time series is described.

FIG. 6 is a view illustrating how changes in various indexes are plotted in time series in the index display section of the monitoring screen.

As illustrated in FIG. 6, changes in the PI ratio and the TOF values thus calculated in Step S103 in FIG. 2 are respectively plotted in time series on the index display section 220. In the graph of PI ratio, the horizontal axis indicates time and the vertical axis indicates the PI ratio. In the TOF graph, the horizontal axis indicates time and the vertical axis is divided into two portions that are upper portion and lower portion. The upper portion of the vertical axis indicates the TOF ratio and the lower portion of the vertical axis indicates the TOF count and the PTC. The TOF count and the PTC, which share the same axis, are distinguishably plotted in different colors and shapes. For example, in the example of FIG. 6, the TOF count is plotted in circle shape, and the PTC is plotted with double circle shape.

In the example of FIG. 6, initially, the PI ratio is small and the TOF ratio is large. This confirms that analgesia and muscular relaxation have not proceeded. The PI ratio increases with time. This confirms that analgesia is proceeding well. Moreover, regarding the TOF, the TOF ratio decreases to zero with time, and then the TOF count becomes zero, whereby the PTC is measured. This confirms that muscular relaxation is proceeding well. The displaying the changes in the various indexes in time series allows the user to visually evaluate trends of the changes of the indexes, the changes in the states of analgesia, and the like, whereby the user can evaluate the conditions of the patient more surely.

<Modification 2>

Moreover, the index output device 100 may display, on the index display section 220, at least two of the BIS, TOF, and PI ratios by plotting the at least two of them in time series on a 2-dimensional coordinate system including a first axis and a second axis. In the following, an example in which the values of various indexes are plotted in time series on the 2-dimensional coordinate system is described.

FIG. 7 is a view illustrating how values of various indexes are plotted in time series on the 2-dimensional coordinate system in the index display section of the monitoring screen.

As illustrated in FIG. 7, on the index display section 220, the values of the TOF and BIS thus calculated are plotted in time series on the 2-dimensional coordinate system in which the horizontal axis is the TOF and the vertical axis is the BIS. The horizontal axis is divided into two portions. Of the two portions, the one on the right side in FIG. 7 indicates the TOF ratio (0% to 100%), and the other one on the left side in FIG. 7 indicates the TOF counts (0 to 4). The vertical axis indicates the BIS (0 to 100). The dotted line L1 indicates a threshold for evaluating the value of the TOF. When the plot is on the left side with respect to the dotted line L1, the dotted line L1 indicates that the muscular relaxation is sufficient. The dotted line L2 indicates a threshold for evaluating the value of the BIS. When the plot is below the dotted line L2, this indicates that the sedation is sufficient. With this configuration, the user can judge the muscular relaxation and the sedation as being sufficient, when the plots are located within the frame formed by the dotted line L1, the dotted line L2, the horizontal axis, and the vertical axis. Moreover, when a plot is out of the frame, the user can make such a decision as to additionally perform a treatment of the muscular relaxation or the sedation.

In the example of FIG. 7, the plot on the right upper portion in FIG. 7 indicates an initial value of the index, and the positions of plots move left-and-downward with time. The plot in double circle located at the leftmost and lowest position indicates a newest value of the index. Moreover, the plotting is displayed with different colors (color densities) depending on the proceeding time from calculation timing of the index. A plot against a shorter proceeding time from the calculation timing of the index, that is, a newer plot is displayed with thicker color (color density). With this configuration, the user can easily evaluate the change in the index.

The presently disclosed subject matter is not limited to the embodiment and modifications mentioned above, and can be modified in various ways within the scope of Claims.

For example, although the PI ratio is calculated as the maximum value of the pulse wave amplitude and the minimum value of the pulse wave amplitude in the embodiment above, the calculation method of the PI ratio is not limited to this. For example, the PI ratio may be calculated such that the pulse wave amplitude at the normal time corresponding to the PI at the normal time is measured in advance and stored in the storage 140, and the PI ratio is measured as a ratio between the pulse wave amplitude thus stored and the minimum value of the pulse wave amplitude thus acquired. In this case, it is not necessary to acquire the pulse wave amplitude at the normal time, every time, thereby making it possible to simplify the process.

As an alternative, a pulse wave amplitude measured at a forehead or the like site which is hardly influenced by the pain caused by the TOF stimuli may be used as the pulse wave amplitude at the normal time corresponding to the PI at the normal time. The index output device 100 can acquire SpO2 at two sites such as a fingertip and the forehead, as illustrated in FIG. 4. Therefore, the PI ratio may be calculated as a ratio between the pulse wave amplitude acquired at the forehead and the pulse wave amplitude acquired at the fingertip under the TOF stimulus.

Moreover, although the embodiment above describes the axes of the various indexes displayed on the index display section 220 as axes indicating the range of the minimum values to the maximums values of the various indexes with uniform scaling, the displaying method of the axes is not limited to this. For example, the axes may indicate a predetermined range of various indexes, for example a range from 20 to 80 for the BIS. As an alternative, an axis indicating a value indexed from the index by a predetermined processing, a logarithmic axis, or the like may be used.

Moreover, although the embodiment above describes that the screens illustrated in FIGS. 5 to 7 are selectively displayed on the index display section 220, the screens are not limited to this. Two or more of the screens illustrated in FIGS. 5 to 7 may be displayed at the same time, or the screens illustrated in FIGS. 5 to 7 may be displayed by being switched over according to an operation by the user, or the like.

Moreover, the display methods of the various indexes illustrated in FIGS. 5 to 7 are not display methods independent from each other and may be combined as appropriate. For example, the screen of FIG. 5 may be modified as in the screen of FIG. 7 in such a way that the plots for previous values are displayed with different colors, color densities, shapes, and/or the like, in order to indicate the change of the indexes with time. As an alternative, the diagram showing the thresholds as illustrated in the screen of FIG. 7 may be applied to the screens of FIGS. 5 and 6. For example, the screen of FIG. 5 may display, as the graphic showing the thresholds, a triangle formed by connecting thresholds of the various indexes with straight lines, and a straight line extended from a threshold point on the vertical axis in parallel with the horizontal axis may be displayed in FIG. 6. Moreover, as the display method of the axis for the TOF, the display methods as illustrated in FIGS. 5 to 7, and the other well-known display methods may be adopted as appropriate. Moreover, the BIS, TOF, and PI ratio may be displayed on the index display section 220 in combination with the other index.

Moreover, although the embodiment above describes an example in which the two indexes are plotted on the 2-dimensional coordinate system on the index display section 220 illustrated in FIG. 7, the plotting is not limited to this. For example, three indexes may be displayed by plotting the three indexes on a 3-dimensional coordinate system.

Moreover, although the embodiment above describes that the index output device 100 includes the display section 150 and outputs the various indexes by displaying the various indexes on the display section 150, the output method of the various indexes is not limited to this. For example, the index output device 100 may output the various indexes by transmitting information representative of the various indexes to another device in order to display the various indexes on a displayed device provided to the another device.

Although the embodiment above describes that the index output device 100 displays the various indexes and the conditions of the patient are confirmed and determined when the user checks the indexes thus displayed, the index output device is not limited to this. For example, the index output device 100 may be configured to determine the conditions of the patient on the basis of predetermined thresholds of the various indexes. For example, the index output device 100 may be configured to determine that the patient is under sedation, if the BIS is below the predetermined threshold, and to notify the user that the patient is under sedation. As an alternative, the index output device 100 may be configured to notify that the patient is not under sedation, when the BIS exceeds above the predetermined threshold.

The means and methods for performing various processes in the index output device according to the embodiment above can be realized either by dedicated hardware circuits or by a programmed computer. The program may be provided via a computer readable recording medium such as a flexible disc, CD-ROM, or the like, or may be provided in an online way via a network such as the Internet. In this case, the program stored in computer readable recording medium is forwarded to a storage section such as a hard disc, and stored in the storage section. Moreover, the program may be provided as a single application soft, or may be incorporated in software of the index output device as one function of the index output device.

The present application is based on Japanese Patent Application No. 2016-032385 filed on Feb. 23, 2016, and the entire content disclosed therein is incorporated herein by reference.

The invention claimed is:
1. An index output device comprising:
an electric stimulation section comprising at least one electrode configured to apply an electric stimulus for monitoring level of muscular relaxation utilizing Train of Four (TOF) to a living body;
an acquisition section comprising at least one sensor configured to acquire a plurality of physiological responses from the living body in response to the electric stimulus applied to the living body by the electric stimulation section, the plurality of physiological responses including pulse waves;
a calculation section comprising a CPU configured to calculate, based on the plurality of responses of the living body acquired by the acquisition section, an index related to a level of muscular relaxation and an index related to a level of analgesia; and
an output section comprising a display configured to output the calculated indexes;
wherein the calculation section calculates the index related to the level of analgesia on the basis of a ratio between a pulse wave amplitude of the pulse waves at a time without the electric stimulus and a pulse wave amplitude of the pulse waves at a time when the electric stimulus is applied; and
wherein the output section is configured to plot the indexes along axes extended in different directions from a common start point, and to display a shape formed by connecting the plotted indexes.

2. The index output device according to claim 1, wherein the acquisition section is configured to further acquire brain waves of the living body, and the calculation section is configured to further calculate an index related to a level of sedation from the acquired brain waves.

3. The index output device according to claim 1, wherein the output section performs the plotting in such a way that the index related to the level of analgesia calculated by the calculation section is plotted on an axis on which a point further from the start point indicates a smaller value, and the index related to the level of muscular relaxation is plotted on an axis on which a point further from the start point indicates a lower level of muscular relaxation.

4. The index output device according to claim 1, wherein the output section is configured to display a change of each index calculated by the calculation section, by plotting each index_in time series.

5. The index output device according to claim 1, wherein the output section is configured to display the calculated indexes by plotting the indexes in time sequence on a coordinate system having a first axis and a second axis extended in a direction different from that of the first axis, the first axis being for a first index of the calculated indexes, and the second axis being for a second index of the calculated indexes.

6. The index output device according to claim 1, wherein the output section is configured to display, together with the plotting, a diagram corresponding to a threshold for evaluating values of the indexes plotted.

7. The index output device according to claim 2, wherein the output section is configured to plot the three indexes along axes extended in different directions from a common start point, and to display a triangle formed by connecting the plotted indexes.

8. An index output method comprising the steps of:
applying an electric stimulus through at least one electrode to a living body for monitoring level of muscular relaxation utilizing Train of Four (TOF);
acquiring through at least one sensor a plurality of physiological responses from the living body in response to the electric stimulus applied to the living body in the step of applying, the plurality of physiological responses including pulse waves;

calculating through a CPU, from the plurality of responses of the living body acquired in the step of acquiring, an index related to a level of muscular relaxation and an index related to a level of analgesia; and outputting through a display the indexes calculated in the step of calculating;

wherein the CPU calculates the index related to the level of analgesia on the basis of a ratio between a pulse wave amplitude of the pulse waves at a time without the electric stimulus and a pulse wave amplitude of the pulse waves at a time when the electric stimulus is applied; and wherein the display is configured to plot the indexes along axes extended in different directions from a common start point, and to display a shape formed by connecting the plotted indexes.

9. A non-transitory recording medium storing a computer-readable index output program for causing a computer to perform the steps of:

applying an electric stimulus through at least one electrode to a living body for monitoring level of muscular relaxation utilizing Train of Four (TOF);

acquiring a plurality of physiological responses through at least one sensor from the living body in response to the electric stimulus applied to the living body in the step of applying, the plurality of physiological responses including pulse waves;

calculating through a CPU, from the plurality of responses of the living body acquired in the step of acquiring, an index related to a level of muscular relaxation and an index related to a level of analgesia; and outputting through a display the indexes calculated in the step of calculating;

wherein the CPU calculates the index related to the level of analgesia on the basis of a ratio between a pulse wave amplitude of the pulse waves at a time without the electric stimulus and a pulse wave amplitude of the pulse waves at a time when the electric stimulus is applied; and wherein the display is configured to plot the indexes along axes extended in different directions from a common start point, and to display a shape formed by connecting the plotted indexes.

* * * * *